United States Patent
Mars et al.

(10) Patent No.: US 9,023,483 B2
(45) Date of Patent: May 5, 2015

(54) WOOD PRESERVATIVE COMPOSITIONS USEFUL FOR TREATING COPPER-TOLERANT FUNGI

(75) Inventors: Craig Andrew Mars, Eggborough (GB); David Grindon Cantrell, Osbaldwick York (GB); Kevin Hughes, Pontefract (GB); Andrew Stewart Hughes, Pontefract (GB)

(73) Assignee: Arch Timber Protection Limited, Castleford, West Yorkshire (GB)

(*) Notice: Subject to any disclaimer, the term of this patent is extended or adjusted under 35 U.S.C. 154(b) by 104 days.

(21) Appl. No.: 13/805,794

(22) PCT Filed: Jun. 21, 2011

(86) PCT No.: PCT/GB2011/000930
§ 371 (c)(1),
(2), (4) Date: Mar. 6, 2013

(87) PCT Pub. No.: WO2011/161404
PCT Pub. Date: Dec. 29, 2011

(65) Prior Publication Data
US 2013/0209823 A1 Aug. 15, 2013

(30) Foreign Application Priority Data
Jun. 21, 2010 (GB) .................................. 1010439.6

(51) Int. Cl.
*A01N 33/12* (2006.01)
*A01N 43/653* (2006.01)
*B27K 3/00* (2006.01)
*B27K 3/20* (2006.01)
*B27K 3/34* (2006.01)

(52) U.S. Cl.
CPC .............. *A01N 33/12* (2013.01); *A01N 43/653* (2013.01); *B27K 3/002* (2013.01); *B27K 3/20* (2013.01); *B27K 3/343* (2013.01)

(58) Field of Classification Search
USPC ................... 428/532, 537.1, 535, 536, 537.5; 427/393
IPC ........................................................ A01N 33/12
See application file for complete search history.

(56) References Cited

U.S. PATENT DOCUMENTS

| | | | |
|---|---|---|---|
| 4,839,373 A | 6/1989 | Ito et al. | |
| 4,929,454 A | 5/1990 | Findlay et al. | |
| 4,950,685 A | 8/1990 | Ward | |
| 5,248,450 A | 9/1993 | Metzner et al. | |
| 5,385,926 A | 1/1995 | Ludwig et al. | |
| 5,407,920 A | 4/1995 | Dawson | |
| 5,804,591 A | 9/1998 | Valcke et al. | |
| 5,874,025 A | 2/1999 | Heuer et al. | |
| 5,972,971 A | 10/1999 | Heuer et al. | |
| 5,977,168 A | 11/1999 | Konishi et al. | |
| 5,990,043 A | 11/1999 | Kugler et al. | |
| 6,211,218 B1 | 4/2001 | Goettsche et al. | |
| 6,242,440 B1 | 6/2001 | De Witte et al. | |
| 6,248,761 B1 | 6/2001 | Fujimoto | |
| 6,323,224 B1 | 11/2001 | Tsuboi et al. | |
| 6,521,288 B2 | 2/2003 | Laks et al. | |
| 6,558,685 B1 | 5/2003 | Kober et al. | |
| 6,936,624 B2 | 8/2005 | Tsuboi et al. | |
| 7,307,070 B2 | 12/2007 | Heuer et al. | |
| 7,323,187 B1 | 1/2008 | Schur | |
| 7,632,567 B1 | 12/2009 | Zhang et al. | |
| 2001/0000184 A1 | 4/2001 | Konishi et al. | |
| 2001/0051649 A1 | 12/2001 | Heuer et al. | |
| 2003/0010956 A1 | 1/2003 | Las et al. | |
| 2004/0211721 A1 | 10/2004 | Stamets | |
| 2004/0258768 A1 | 12/2004 | Richardson et al. | |
| 2004/0258838 A1 | 12/2004 | Richardson et al. | |
| 2005/0080089 A1 | 4/2005 | Tiedink et al. | |
| 2005/0227956 A1 | 10/2005 | Wang et al. | |
| 2006/0112850 A1 | 6/2006 | Zhang et al. | |
| 2006/0251915 A1 | 11/2006 | Jin et al. | |
| 2006/0252847 A1 | 11/2006 | Hayward et al. | |
| 2006/0257578 A1 | 11/2006 | Zhang et al. | |
| 2006/0269583 A1 | 11/2006 | Garst et al. | |
| 2006/0276468 A1 | 12/2006 | Blow | |
| 2007/0021385 A1 | 1/2007 | Zhang et al. | |
| 2007/0082187 A1 | 4/2007 | Wang et al. | |
| 2007/0142410 A1 | 6/2007 | Garnier | |
| 2007/0151476 A1 | 7/2007 | Humar et al. | |
| 2008/0046277 A1 | 2/2008 | Stamets | |
| 2008/0108680 A1 | 5/2008 | Bruns et al. | |
| 2008/0132569 A1 | 6/2008 | Chang et al. | |
| 2008/0187669 A1 | 8/2008 | Kingma et al. | |
| 2008/0193640 A1 | 8/2008 | Zhang et al. | |
| 2009/0203643 A1 | 8/2009 | Patel | |
| 2009/0280185 A1 | 11/2009 | Richardson et al. | |
| 2010/0068545 A1 | 3/2010 | Zhang et al. | |
| 2011/0030579 A1 | 2/2011 | Koop et al. | |

FOREIGN PATENT DOCUMENTS

| | | | |
|---|---|---|---|
| AU | 2007/0203237 A1 | | 2/2008 |
| CA | 2238033 A1 | | 5/1997 |
| CN | 1633853 A | | 7/2005 |
| EP | 2036435 | * | 3/2009 |
| EP | 2036435 A1 | | 3/2009 |
| JP | 2003/252705 A | | 9/2003 |
| WO | 93/02557 A1 | | 2/1993 |
| WO | WO93/02557 | * | 2/1993 |
| WO | 97/18713 A1 | | 5/1997 |
| WO | WO97/18713 | * | 5/1997 |
| WO | 01/28331 A1 | | 4/2001 |
| WO | 2007/053252 A1 | | 5/2007 |

OTHER PUBLICATIONS

Ursula Kues, "Wood Production, Wood Technology and Biotechnological Impacts", 2007, Universitatsverlag Gottingen, Available online at http://webdoc.sub.gwdg.de/univerlag/2007/wood_production.pdf.

* cited by examiner

Primary Examiner — Leszek Kiliman
(74) Attorney, Agent, or Firm — Lucas & Mercanti, LLP

(57) ABSTRACT

The present invention provides a method of protecting wood or other cellulosic material from decay by copper-tolerant fungi, and wood preservative formulations for use in the same. The wood preservative formulations comprise a biocidal metal compound, a 1,2,4-triazole and a didecyl quaternary ammonium cation. Didecyldimethyl quaternary ammonium compounds are particularly preferred.

34 Claims, No Drawings ial is a 371 of PCT/GB11/00930, filed Jun. 21, 2011, which claims the benefit of British Patent Application No. 1010439.6, filed Jun. 21, 2010, the contents of each of which are incorporated herein by reference.

WOOD PRESERVATIVE COMPOSITIONS USEFUL FOR TREATING COPPER-TOLERANT FUNGI

CROSS-REFERENCE TO RELATED APPLICATIONS

This application is a 371 of PCT/GB11/00930, filed Jun. 21, 2011, which claims the benefit of British Patent Application No. 1010439.6, filed Jun. 21, 2010, the contents of each of which are incorporated herein by reference.

FIELD OF THE INVENTION

The present invention relates to methods for treating naturally occurring copper-tolerant fungi such as *Serpula himantioides, Antrodia* spp. and *Fomitopsis palustris* in order to limit their ability to cause decay of wood and other cellulosic materials. The present invention further relates to formulations which have been found to be particularly effective in treating these fungi.

BACKGROUND OF THE INVENTION

Biocidal copper compounds have been used as wood preservatives for many years. Copper is known to have poor solubility in aqueous systems, and there have been many methodologies developed to ensure that biocidal copper is actually delivered to wood when applied as a wood preservative. The first generation of such formulations utilised soluble copper salts such as copper sulphate and the like, for example Bordeaux mixture. However, these types of systems can have high leaching rates (i.e. the active copper ions are washed away after application). Leaching is unfavourable, since it results in biocidal ions potentially acting as pollutants in waterways, as well as leading to increased costs. To mitigate leaching, copper salts can be administered in combination with a fixing agent such as chromium, such as in chromated-copper-arsenate (CCA). More recently, the use of copper in combination with chromium and arsenate has been restricted in many countries due to the toxicity of chromium/arsenate.

Alternatives to CCA include basic copper carbonate administered in combination with other biocidal ingredients such as quaternary ammonium compounds or biocidal azoles. As reported in WO93/02557, some of these formulations display synergy between the copper and azole, and have therefore found widespread use, as wood preservatives. Commercially available preservatives containing copper-azole mixtures include Tanalith E, available from Arch Timber Protection, Ltd.

More recently, biocidal copper has been administered as micronised copper salts such as copper hydroxide or copper carbonate, which are applied as a suspension of nanoparticles to wood products. As the micronised particles slowly dissolve over time, applying the copper salts in this form allows a steady delivery of the biocidal copper to the wood product.

Other types of biocidal metal ions can also be used to treat wood, such as zinc. Although perhaps not as widespread in its use as copper, there are a number of commercially available wood preservatives which include zinc as a biocidal metal ion. For example, zinc naphthenate is commonly available as "over the counter" brush on wood preservatives. On a commercial scale, ammoniacal copper zinc arsenate (ACZA) has been used for many years. Wood protected with ACZA is available under the trade name Chemonite. Zinc is favourable in some respects as it is relatively non-toxic (at least compared to other biocidal metal ions such as chromium and tin), and often forms colourless complexes.

Copper-organic wood preservatives have been used successfully as a ground contact preservative around the world. However, the applicant has recognised that in certain specific environments, there are some fungi which have proved resistant to such formulations. Although the problems caused by such fungi are uncommon, they can be problematic in certain circumstances. One such fungi is *Serpula himantioides*.

*Serpula himantioides* typically occurs outdoors, usually on coniferous wood although it can rarely occur on wood from deciduous trees. *Serpula himantioides* occurs in warm dry climates, and has been found to be a particular problem for example in grape growing regions such as Portugal, Spain and Southern France. If standard copper-based preservative systems are used to treat, for example, stakes used to support grapevines in these regions, the treated wood may still be prone to decay by *Serpula himantioides*.

Another type of fungi which has proved resistant to standard copper-based treatments are *Antrodia* spp., such as *Antrodia vaillantii, Antrodia sinuosa* and *Antrodia radiculosa*. *A. vaillantii* has been found to occur in temperate climates such as Germany or Austria. For example, telegraph poles treated with copper-chromate based wood preservative formulations have been found to be prone to decay by *Antrodia vaillantii*. One theory put forward to explain the resistance of *Antrodia vaillantii* is that this fungus produces excessive amounts of oxalic acid, which interacts with the copper to prevent it functioning as an effective biocide. Studies have also shown that once an in-ground piece of wood has been infected with *Antrodia vaillantii*, it cannot simply be replaced with a new piece of wood, as the replacement wood is also prone to decay by the *Antrodia vaillantii* fungus.

SUMMARY OF THE INVENTION

There remains a need to develop effective methods for protecting wood against decay by these fungi. The present inventors have found that by adding a didecyl quaternary ammonium compound to a biocidal metal-containing formulation (such as a copper/azole formulation), the formulation offers protection against decay due to copper-tolerant fungi such as *Serpula himantioides* and *Antrodia* spp. This is surprising as these quaternary ammonium compounds themselves provide limited protection against these species. Thus, a surprising synergistic effect is observed between the didecyl quaternary ammonium compound and the primary wood preservative components.

DETAILED DESCRIPTION OF THE INVENTION

Thus, in one aspect, the present invention provides a method for protecting wood or other cellulosic material from decay by copper-tolerant fungi, comprising applying thereto a biocidal metal compound, a 1,2,4-triazole compound and a salt containing a didecyl quaternary ammonium cation. Preferably the three components are applied in a single formulation but they need not be, provided they are applied in a way which provides a combination treatment, i.e. the three active ingredients are present simultaneously in the wood or other substrate.

The present invention also provides a wood preservative formulation comprising a biocidal metal compound, a 1,2,4-triazole compound and didecyldimethyl ammonium carbonate/bicarbonate, preferably didecyldimethyl ammonium carbonate. In such formulations, it is preferred that the amount of carbonate in the formulation as a whole is at least 50% of the amount of didecyldimethylammonium cation.

The present invention also provides a wood preservative formulation comprising a biocidal metal compound, a 1,2,4-triazole, a salt containing a didecyldimethyl ammonium cation, and an isothiazolone. In such formulations, the salt containing the didecyldimethyl ammonium cation is preferably didecyldimethyl ammonium carbonate/bicarbonate.

The present invention also provides a wood preservative formulation comprising a biocidal metal compound, a 1,2,4-triazole compound and compound of formula (I):

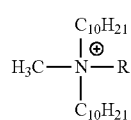
(I)

wherein R denotes $(CH_2CH_2O)_mH$ where m is an integer from 1 to 20 typically from 1 to 8, preferably from 1 to 5 and more preferably from 3 to 5. In such compositions, the preferred counterion to the compound of formula (I) is propionate $(CH_3CH_2CO_2^-)$ or lactate $(CH_3CH(OH)CO_2^-)$, with propionate being the most preferred.

Preferred biocidal metal compounds are selected from biocidal copper compounds, biocidal zinc compounds, and mixtures thereof. Biocidal copper compounds are the most preferred.

By "decay" is meant a process leading to the reduction of mass and structural integrity of the wood or other cellulosic material. The method of the present invention therefore seeks to provide long term protection to wood and other cellulosic materials against the reduction of mass and structural integrity caused by copper-tolerant fungi. The protection of wood or other cellulosic material from decay is distinct from the protection against surface staining and other forms of superficial mould growth, which do not lead to a significant reduction in mass or reduction in the structural integrity of the wood or other cellulosic material. Therefore, the method of the present invention is not intentionally directed at preventing or mitigating the problems that arise due to sapstaining or other surface staining that may occasionally arise with copper-containing wood preservative compositions. Instead, the method of the present invention seeks to enhance the efficacy of copper-containing wood preservatives against certain problematic fungi which cause structural decay of wood or other cellulosic species.

By "copper-tolerant fungi" is meant fungi which are tolerant of copper-based wood preservative formulations. Copper-tolerant fungi lead to more than 3% weight loss in Scots pine sapwood (*Pinus sylvestris*) loaded with 1.5 kg/m³ copper, in the absence of any other biocides, when tested in accordance with EN113. Preferably, copper-tolerant fungi lead to more than 3% weight loss in Scots pine sapwood (*Pinus sylvestris*) loaded with 1 kg/m³ copper and 0.04 kg/m³ tebuconazole, in the absence of any other biocides, when tested in accordance with EN113. Preferred copper-tolerant fungi for treatment according to the present invention include *Serpula himantioides*, *Antrodia* spp. such as *Antrodia vaillantii*, *Antrodia sinuosa* and *Antrodia radiculosa*, *Gloeophyllum abietinum*, *Gloeophyllum sepiarium*, *Paxillus panuodes*, *Stereum hirsutum* and *Fomitopsis palustris*.

Particularly preferred copper-tolerant fungi for treatment according to the present invention include *Serpula himantioides*, *Antrodia* spp. such as *Antrodia vaillantii*, *Antrodia sinuosa* and *Antrodia radiculosa*, *Gloeophyllum abietinum*, *Gloeophyllum sepiarium*, *Paxillus panuodes* and *Stereum hirsutum*. Other species including copper-sensitive species, may be simultaneously treated by the methods of the present invention but the environmental circumstances and/or site history will typically be such as to indicate problems or potential problems of decay caused by copper-tolerant species, such as those mentioned herein.

Both "protection" and "treatment" as used herein are broad terms and cover prevention of or reduction in establishment of fungal populations on the wood or other cellulosic material, as well as inhibition of the growth of existing populations including eradication thereof.

Preferably, the present invention provides a method for protecting wood or other cellulosic material from decay by *Serpula himantioides*, *Antrodia* spp. and *Fomitopsis palustris*, preferably from decay by *Serpula himantioides* and *Antrodia* spp., more preferably from decay by *Serpula himantioides*, *Antrodia vaillantii*, *Antrodia sinuosa* or *Antrodia radiculosa*. Most preferably, the present invention provides a method for protecting wood or other cellulosic material from decay by *Serpula himantioides*.

By "didecyl quaternary ammonium cation" is meant a quaternary ammonium cation in which two of the four substituents on the quaternary nitrogen are n-decyl groups.

Preferred didecyl quaternary ammonium cations for use in the methods of the invention include didecylmethyl quaternary ammonium cations, which have two n-decyl groups and a methyl group on the quaternary nitrogen.

Particularly preferred didecyl quaternary ammonium cations are represented by the compound of formula (I):

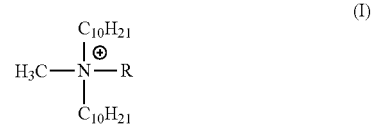
(I)

wherein R denotes methyl or $(CH_2CH_2O)_mH$ where m is an integer from 1 to 20 typically from 1 to 8, preferably from 1 to 5 and more preferably from 3 to 5.

Preferably, the didecyl quaternary ammonium cation is a didecyldimethyl ammonium cation.

In the methods of the invention, the didecyl quaternary ammonium cation (DQA cation) may derive from any suitable didecyl quaternary ammonium salt. Suitable counterions include chloride, carbonate, bicarbonate, methylsulphate, formate, acetate, lactate, propionate and the like.

A particularly preferred DQA cation that can be used in the method of the present invention is the didecyldimethyl ammonium (DDA) cation. Preferred counterions for the DDA cation are selected from chloride, carbonate and bicarbonate. Most preferred are carbonate, bicarbonate and mixtures thereof, with carbonate being the most preferred.

Another particularly preferred DQA salt that can be used in the method of the invention is N,N-didecyl-N-methyl-poly (oxyethyl) ammonium propionate (Bardap-26) or N,N-didecyl-N-methyl-poly(oxyethyl) ammonium lactate, with Bardap-26 being particularly preferred. Bardap-26 corresponds to a mixture of compounds of formula (I) as defined above in which R denotes $(CH_2CH_2O)_mH$ and m is an integer of from 1 to 5. In other words, Bardap-26 corresponds to a compound of formula (I) as defined above wherein R denotes $(CH_2CH_2O)_mH$ and m is a range of integers of from 1 to 5.

The 1,2,4-triazole compound incorporates a five-membered diunsaturated ring composed of three nitrogen atoms and two carbon atoms at non-adjacent positions.

Preferred triazole compounds include a triazole compound selected from compounds of formula (II):

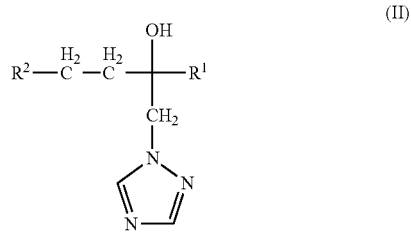

(II)

wherein $R^1$ represents a branched or straight chain $C_{1-5}$ alkyl group (e.g. t-butyl) and $R^2$ represents a phenyl group optionally substituted by one or more substituents selected from halogen (e.g. chlorine, fluorine or bromine) atoms or $C_{1-3}$ alkyl (e.g. methyl), $C_{1-3}$ alkoxy (e.g. methoxy), phenyl or nitro groups.

Alternatively, the triazole compound is advantageously selected from compounds of formula (III):

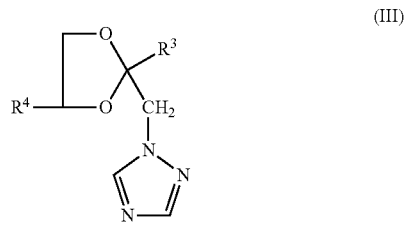

(III)

wherein $R^3$ is as defined for $R^2$ above and $R^4$ represents a hydrogen atom or a branched or straight chain $C_{1-5}$ alkyl group (e.g. n-propyl).

Particularly preferred triazoles include, but are not limited to, triadimefon, triadimenol, triazbutil, propiconazole, cyproconazole, difenoconazole, fluquinconazole, tebuconazole, flusilazole, uniconazole, diniconazole, bitertanol, hexaconazole, azaconazole, flutriafol, epoxyconazole, tetraconazole, penconazole, ipconazole, prothioconazole, metconazole (sometimes referred to as metaconazole) and mixtures thereof.

Even more preferred triazoles are propiconazole, azaconazole, hexaconazole, tebuconazole, cyproconazole, triadimefon, ipconazole, prothioconazole, metconazole and mixtures thereof, preferably propiconazole, tebuconazole, cyproconazole and mixtures thereof, more preferably propiconazole, tebuconazole and mixtures thereof, with mixtures of propiconazole and tebuconazole being the most preferred. In the most preferred embodiment, propiconazole and tebuconazole are used in mixture in a ratio of propiconazole:tebuconazole of 1:10 to 10:1, preferably 1:5 to 5:1 by weight.

In some embodiments, particularly when used in combination with N,N-didecyl-N-methyl-poly(oxyethyl) ammonium cations such as Bardap-26 and the like, particularly preferred triazoles are selected from difenoconazole, triadimefon, metconazole, cyproconazole, propiconazole and tebuconazole. Preferred 1,2,4-triazoles are selected from cyproconazole, propiconazole and tebuconazole, with cyproconazole being the most preferred 1,2,4-triazole. The biocidal metal compound (such as a biocidal copper compound) may be present in a form such that metal ions are free in solution or may form part of a complex. Similarly, the 1,2,4-triazole compound may be free in solution or may be present in the form of a salt or complex. For example, the 1,2,4-triazole compound may be present in the form of a complex with the biocidal metal ion (such as the biocidal copper ion).

In preferred embodiments, the biocidal metal ion is a biocidal copper ion. The biocidal copper may advantageously be incorporated into the formulation in the form of inorganic copper salts, such as carbonate, bicarbonate, sulphate, nitrate, chloride, hydroxide, borate, fluoride or oxide. Alternatively, the copper may be in the form of a simple organic salt, such as formate or acetate, or as a complex such as N-nitroso-N-cyclohexyl-hydroxylamine-copper (copper-HDO) or copper pyrithione (bis(2-pyridylthio)copper 1,1'-dioxide, CAS number 14915-37-8).

Preferably, the biocidal copper ion is a copper (II) ion. Preferred forms of copper (II) include basic copper carbonate ($CuCO_3.Cu(OH)_2$), copper (II) acetate, copper (II) hydroxide, copper (II) oxide and copper (II) sulphate pentahydrate, with basic copper carbonate being the most preferred. Preferred copper (I) compounds that can be used are copper (I) oxide and copper-HDO.

Particularly preferred biocidal copper compounds are selected from basic copper carbonate, copper (II) acetate, copper (II) sulphate pentahydrate, copper (II) hydroxide, copper (II) oxide, copper (I) oxide, and copper-HDO.

In some preferred embodiments, the biocidal metal ion may be a biocidal zinc ion. The biocidal zinc may advantageously be incorporated into the formulation in the form of inorganic zinc salts, such as carbonate, bicarbonate, hydroxide, borate, oxide or phosphate. Alternatively, the zinc may be in the form of a an organozinc compound such as a simple organic salt, such as formate or acetate, or as a complex such as N-nitroso-N-cyclohexyl-hydroxylamine-zinc (zinc-HDO), zinc naphthenate or zinc pyrithione (bis(2-pyridylthio)zinc 1,1'-dioxide-CAS number 13463-41-7).

Preferred zinc compounds include zinc oxide, zinc carbonate, zinc borate and zinc pyrithione, with zinc oxide, zinc carbonate and zinc borate being the most preferred.

The biocidal metal compound may be in the form of dispersed particles, such as micronised particles. In such dispersed (e.g. micronised) particles, preferably 95% by weight of the metal salt has a particle size below 1 μm, more preferably 99% by weight of the metal salt has a particle size below 1 μm. Even more preferably, 95% by weight of the metal salt has a particle size below 0.5 μm, more preferably 99% by weight of the metal salt has a particle size below 0.5 μm. Particle size may be measured by Stokes law settling (which may be assisted by centrifugation) down to about 0.2 μm, and by dynamic light (X-ray) scattering or by Doppler light scattering at smaller particle sizes.

Dispersed particles may be formed by a number of methods, such as by precipitation methods or by milling. Preferably, the dispersed (or micronised) particles are formed by wet milling, for example by wet milling in a rotary sand grinder with partially stabilised zirconia beads having a diameter of 0.5 mm at, for example, 1000 rpm.

As an alternative, the metal may be included in the formulation of the invention as a solubilised metal ion. Suitable methods for solubilising metal ions such as copper and zinc are known in the art, for example from WO93/02557. Suitable complexing agents for the copper or zinc ion include, for example, polyphosphoric acids such as tripolyphosphoric acid; ammonia; water soluble amines and alkanolamines capable of complexing with copper or zinc cations; aminocarboxylic acids such as glycine, glutamic acid, ethylenediaminetetraacetic acid (EDTA), hydroxyethyldiamine triacetic acid, nitrilotriacetic acid and N-dihydroxy ethylglycine; polymeric compounds which contain groups capable of complexing with metallic cations such as polyacrylic acids; hydroxycarboxylic acids such as tartaric acid, citric acid, malic acid, lactic acid, hydroxybutyric acid, glycollic acid, gluconic acid and glucoheptonic acid; long chain or "fatty" carboxylic acids such as octanoic acid, decanoic acid, and neodecanoic acid (versatic acid) (these are particularly useful when the biocidal metal ion is zinc); and phosphonic acids such as nitrilotrimethylene phosphonic acid, ethylenediaminetetra (methylene phosphonic acid) and hydroxyethylidene diphosphonic acid. Where the complexing agents are acidic in nature they may be employed either as free acids or as their alkali metal or ammonium salts. These complexing agents may be used either alone or in combination with each other. Preferred complexing agents are selected from alkanolamines, such as monoethanolamine, diethanolamine, triethanolamine, monopropanolamine, dipropanolamine, and tripropanolamine. Ethanolamines are preferred, with monoethanolamine being particularly preferred.

In some embodiments of the present invention, it is preferred to use a solution that is free of ammonia or alkanolamine (i.e. alkanes that have both hydroxy (OH) and amino ($NH_2$, $NHR$, $NR_2$) functional groups). This is particularly the case where dispersed (or micronised) biocidal metal compounds are used.

In preferred embodiments, the formulations used in the method of the invention (and the formulations of the invention) additionally include an isothiazolone. Preferred isothiazolones include, but are not limited to, methylisothiazol-3-one (MIT), 5-chloro-2-methyl-4-isothiazolin-3-one (CMIT), 4,5-dichloro-2-n-octyl-4-isothiazolin-3-one (DCOIT), octylisothiazol-3-one (OIT), 1,2-benzisothiazol-3(2H)-one (BIT), N-methyl-1,2-benzisothiazol-3-one (MBIT) and N-(n-butyl)-1,2-benzisothiazol-3-one (BBIT). Preferred isothiazolones are CMIT, OIT, BIT and BBIT, with OIT being the most preferred. Suitably, the formulations used in the method of the invention can be prepared by adding an emulsified formulation of the 1,2,4-triazole compound to an aqueous solution of a biocidal metal (such as copper) salt and a DQA salt. Alternatively, formulations can be prepared using only organic solvents. To prepare such formulations, a biocidal metal (such as copper) salt of a carboxylic acid (such as decanoic or octanoic acid) is prepared and dissolved in a suitable organic solvent to form a concentrate. The 1,2,4-triazole compound and DQA salt can then be added directly to the concentrate with a suitable solvent, which may be an aromatic or aliphatic hydrocarbon solvent such as white spirit, petroleum distillate, kerosene, diesel oils, naphthas, glycol ethers, benzyl alcohol, 2-phenoxy ethanol, methyl carbitol, propylene carbonate, benzyl benzoate, ethyl lactate and 2-ethyl hexyl lactate.

It is clear that in some instances it is preferable to prepare the formulation from two or even three separate concentrated formulations shortly before administration. Thus, the formulation may be produced by mixing a composition comprising, for example, a 1,2,4-triazole and a biocidal metal (such as copper) salt together with a composition comprising a DQA salt, then diluting the resultant mixture prior to applying to a substrate. Preferably, the formulation of the invention may be formulated by mixing a formulation containing a DQA salt with a wood preservative formulation comprising a 1,2,4-triazole and a biocidal metal (such as copper) salt.

Preferably, the weight ratio of biocidal metal (such as copper) ion to 1,2,4-triazole in the formulation of the invention is from 1:1 to 250:1; more preferably from 2.5:1 to 100:1; even more preferably from 10:1 to 50:1. The weight ratio of biocidal metal (such as copper) ion to DQA (as DDA carbonate) is preferably in the range of 0.01:1 to 100:1; more preferably 0.05:1 to 50:1.

Conveniently, the formulations of the present invention are applied as a liquid formulation. They may also be applied as a solid implant, paste or dispersion containing micronised biocidal particles. Preferably, the formulations are applied as a liquid formulation, e.g. in the form of an emulsion made up of solubilised liquid droplets which do not contain any biocides in a solid, particulate form. Preferably, the emulsions are in the form of a micro-emulsion. The person skilled in the art of making emulsions knows how to make an emulsion according to the invention by the use of suitable solvents and emulsifying agents.

The application of these formulations may be by one or more of dipping, deluging, spraying, brushing or other surface coating means or by impregnation methods, e.g. high pressure or double vacuum impregnation into the body of the wood or other material, all being techniques well known to the man skilled in the art. Impregnation under pressure is particularly advantageous when the substrate is wood or a wood composite material which is made to become wet during its life, for example, wood for window frames, timber used above ground in exposed environments such as decking and timber used in ground contact or fresh water or salt water environments.

The formulation is preferably applied to the wood (or other cellulosic material) such that the level of biocidal metal (such as copper) retention in the wood is preferably up to 10 kg/m$^3$, more preferably from 1 to 5 kg/m$^3$. Likewise, the amount of didecyl quaternary ammonium cation retained in the wood in the method of the invention, expressed as kilograms of didecyl quaternary ammonium carbonate per cubic meter of wood, is at least 0.1 kg/m$^3$, preferably at least 0.5 kg/m$^3$, for example from 0.5 to 10 kg/m$^3$, more preferably from 0.5 to 5 kg/m$^3$.

Wood or other cellulosic materials products which have been treated with a formulation or by a method according to the invention as described herein, comprise further aspects of the present invention. Additionally, wood or other cellulosic materials comprising or impregnated with a formulation according to the invention comprise a further aspect of the present invention.

Types of wood or other cellulosic materials which can benefit from treatment with the formulations of the invention include sawn timber, logs, glulam, plywood, laminated veneer lumber, wood based composite products such as oriented strandboard, medium density fibreboard, fibreboard, hardboard, and particle board, cotton, hessian, rope and cordage. Preferred are sawn timber, logs, glulam, plywood, laminated veneer lumber, wood based composite products such as oriented strandboard, medium density fibreboard, fibreboard, hardboard and particle board, with sawn timber, logs and plywood being particularly preferred, with the most preferred being sawn timber and logs.

Particularly preferred types of timber that are treated in the method of the invention include wooden telegraph poles, wooden stakes, wooden fence poles and wooden fencing.

The present invention also provides a method of preventing copper-tolerant fungi such as *Serpula himantioides, Antrodia* spp., *Gloeophyllum abietinum, Gloeophyllum sepiarium, Paxillus panuodes, Stereum hirsutum* and *Fomitopsis palustris* (preferably *Serpula himantioides, Antrodia* spp., *Gloeophyllum abietinum, Gloeophyllum sepiarium, Paxillus panuodes* and *Stereum hirsutum*) from growing on a wood or other cellulosic material, said method comprising applying to the wood or other cellulosic material a biocidal metal (such as copper) compound, a 1,2,4-triazole compound and a salt containing a didecyl quaternary ammonium cation.

The present invention also provides a method of preventing *Serpula himantioides* from growing on a wood or other cellulosic material, said method comprising applying to the wood or other cellulosic material a biocidal metal (such as copper) compound, a 1,2,4-triazole compound and a salt containing a didecyl quaternary ammonium cation.

The present invention also provides a method of preventing *Antrodia* spp. such as *Antrodia vaillantii*, *Antrodia sinuosa* or *Antrodia radiculosa* from growing on a wood or other cellulosic material, said method comprising applying to the wood or other cellulosic material a biocidal metal (such as copper) compound, a 1,2,4-triazole compound and a salt containing a didecyl quaternary ammonium cation.

The present invention also provides the use of a salt containing a didecyl quaternary ammonium cation to enhance the efficacy of a wood preservative formulation containing a biocidal metal (such as copper) compound and a 1,2,4-triazole against copper-tolerant fungi such as *Serpula himantioides*, *Antrodia* spp., *Gloeophyllum abietinum*, *Gloeophyllum sepiarium*, *Paxillus panuodes*, *Stereum hirsutum* and *Fomitopsis palustris* (preferably *Serpula himantioides*, *Antrodia* spp., *Gloeophyllum abietinum*, *Gloeophyllum sepiarium*, *Paxillus panuodes* and *Stereum hirsutum*)

The present invention also provides the use of a salt containing a didecyl quaternary ammonium cation to enhance the efficacy of a wood preservative formulation containing a biocidal metal (such as copper) compound and a 1,2,4-triazole against *Serpula himantioides* and/or *Antrodia* spp. such as *Antrodia vaillantii*, *Antrodia sinuosa* or *Antrodia radiculosa*.

The method of the present invention preferably comprises the additional step of positioning the treated wood or other cellulosic material at a locus where spores of copper-tolerant fungii (for example *Antrodia* spp. such as *Antrodia vaillantii*) are present. In other words, the method of the present invention preferably includes, as a subsequent step after the step of applying the biocidal components to the wood or other cellulosic material, the step of positioning or placing the treated wood or other cellulosic material in the ground at a location which has a history of growth of copper-tolerant fungi (for example *Antrodia* spp. such as *Antrodia vaillantii*) or where spores of such fungi may be present.

The invention will now be further described with reference to the following non-limiting Examples.

EXAMPLES

Example 1

In line with the EN 113 protocol, samples of pine (*Pinus sylvestris*) sapwood (dimensions 50×25×15 mm) were oven dried and their mass accurately recorded. The blocks were then impregnated with various wood preservative formulations using a vacuum pressure cycle to ensure full penetration, re-weighed to determine the uptake of the fluid followed by drying at room temperature, in accordance with EN 113. After drying, the blocks were water leached according to the EN84 protocol.

A decay test was used using *Serpula himantioides* strain ATCC 64894. The procedure adopted was as follows: Magenta® GA-7 was used as a culture vessel. Each jar was filled with 130 cm³ of 2% MEA amended with 0.05% CaNO₃ and autoclaved. After the jars had solidified, 20 cm³ of 2% MEA amended with 0.1% CaHPO₄ was added on top of the solid agar to each jar in the Laminar flow hood. After fungal inoculum was added, the jars were placed in an incubator (25° C., 75% RH). When fungal hyphae covered the surface of agar, two of the treated wood blocks were placed into each jar. Five replicates were made per each treatment. The samples were collected after 16 weeks of exposure and weight loss was calculated.

The various formulations which were impregnated into the wood were as follows:

| Copper solution | % Active Ingredient | Weight percent |
|---|---|---|
| Basis copper carbonate | 46 | 19.57 |
| Monoethanolamine | 90 | 33.64 |
| Water | | 46.79 |

| Azole solution | % Active Ingredient | Weight percent |
|---|---|---|
| Tebuconazole | 93 | 10.75 |
| Ethoxylated coco amine surfactant | 100 | 89.25 |

| Mixed Azole solution | % Active Ingredient | Weight percent |
|---|---|---|
| Propiconazole | 50 | 10.00 |
| Tebuconazole | 93 | 5.38 |
| Ethoxylated coco amine surfactant | 100 | 84.62 |

As shown in the above tables, the copper composition contains about 9% by weight copper, while both of the azole compositions contain about 10% by weight azole. The DQA cation was applied to the wood as a solution of 50 weight percent didecyldimethyl ammonium carbonate (DDACarbonate). The actual retention of the active ingredients in each of the samples together with the average weight loss after exposure for 16 weeks is described in the Table below:

| Product | Cu Retention (kg/m³) | DDACarbonate Retention (kg/m³) | 16 weeks of exposure Average of Weight Loss (%) |
|---|---|---|---|
| Cu:tebuconazole, 25:1 | 1.03 | | 15.43 (3.14) |
| | 2.64 | | 11.89 (1.87) |
| | 3.33 | | 5.33 (3.49) |
| | 4.25 | | 8.14 (1.63) |
| Cu:tebuconazole/ propiconazole, 25:1 | 0.92 | | 16.30 (3.65) |
| | 2.29 | | 9.92 (1.86) |
| | 3.04 | | 8.17 (2.40) |
| | 4.03 | | 2.86 (1.90) |
| Cu:tebuconazole, 25:1 + DDACarbonate | 2.6 | 1.9 | 0.28 (0.30) |
| Cu:tebuconazole, 25:1 + DDACarbonate | 2.6 | 3.79 | 0.10 (0.21) |
| Cu:tebuconazole/ propiconazole, 25:1 + DDACarbonate | 2.62 | 1.91 | 0.04 (0.08) |
| Cu:tebuconazole/ propiconazole, 25:1 + DDACarbonate | 2.64 | 3.86 | 0.06 (0.11) |
| CCA | 15.76 as CCA | | 3.05 (0.33) |

The data in the Table clearly show that even at high copper retention levels, wood treated with copper/azole mixtures is susceptible to decay by *Serpula himantioides*. However, use of copper/azole in combination with DDACarbonate greatly improves the resistance of wood to decay by this fungus.

Example 2

Using a similar procedure to Example 1, wood blocks were impregnated with wood preservative formulations and exposed to various copper-tolerant strains using the decay test described above. The wood samples were exposed for 13 weeks.

The actual retention of the active ingredients in each of the samples together with the average weight loss after exposure for 13 weeks is described in the Table below:

| Product | Cu Retention (Kg/m³) | DDACarbonate Retention (Kg/m³) | 13 weeks of exposure Average weight loss % | | |
|---|---|---|---|---|---|
| | | | *Antrodia sinuosa* | *Antrodia vaillantii* | *Fomitopsis palustris* |
| Cu:teb./prop. 25:1 | 1.5 | 0 | 24.07 | 14.87 | 13.94 |
| Cu:teb./prop. 25:1 + DDACarbonate | 1.5 | 1 | 8.25 | 5.50 | 6.04 |

The data in the table show that the addition of DDACarbonate to the copper/azole mixtures greatly improves the protection against the copper-tolerant fungi.

Example 3

Using a similar procedure to Example 1, wood blocks were impregnated with various wood preservative formulations and exposed to *Serpula himantioides* using the decay test described above. The wood samples were exposed for 16 weeks.

The actual retention of the active ingredients in each of the samples together with the average weight loss relative to the untreated controls after exposure for 16 weeks is described in the Table below:

| Product | Cu Retention (Kg/m³) | DDACarbonate Retention (Kg/m³) | 16 weeks of exposure Average weight loss % of untreated weight loss |
|---|---|---|---|
| Untreated | 0 | 0 | 100 |
| DDACarbonate | 0 | 0.25 | 84 |
| Cu:teb./prop. 25:1 + DDACarbonate | 1 | 0.25 | 50 |
| Cu:teb./prop. 25:1 + DDACarbonate | 1.5 | 0.25 | 48 |
| Cu:teb./prop. 25:1 + DDACarbonate | 2 | 0.25 | 22 |
| Untreated | 0 | 0 | 100 |
| DDACarbonate | 0 | 0.5 | 67 |
| Cu:teb./prop. 25:1 + DDACarbonate | 1 | 0.5 | 9 |
| Cu:teb./prop. 25:1 + DDACarbonate | 1.5 | 0.5 | 10 |
| Cu:teb./prop. 25:1 + DDACarbonate | 2 | 0.5 | 0 |
| Untreated | 0 | 0 | 100 |
| DDACarbonate | 0 | 0.5 | 67 |
| Cu:teb. 25:1 + DDACarbonate | 1 | 0.5 | 12 |
| Cu:teb. 25:1 + DDACarbonate | 1.5 | 0.5 | 6 |
| Cu:teb. 25:1 + DDACarbonate | 2 | 0.5 | 0 |
| Untreated | 0 | 0 | 100 |
| DDACarbonate | 0 | 0.5 | 67 |
| Cu:prop. 25:1 + DDACarbonate | 1 | 0.5 | 26 |
| Cu:prop. 25:1 + DDACarbonate | 1.5 | 0.5 | 12 |
| Cu:prop. 25:1 + DDACarbonate | 2 | 0.5 | 11 |

In all the tests, the combination of DDACarbonate and copper/azole formulation provided excellent protection against *Serpula himantioides*, even though DDACarbonate provided relatively little protection against this fungus when used alone.

Example 4

Using a similar procedure to Example 1, 20×20×19 mm wood blocks were impregnated with various wood preservative formulations and exposed to *Antrodia sinuosa* using the decay test described above. The wood samples were exposed for 6 weeks.

The actual retention of the active ingredients in each of the samples together with the average weight loss relative to the untreated controls after exposure for 6 weeks is described in the Table below:

| Formulation | kg/m³ Copper | Cu:azole ratio | kg/m³ Bardap 26 | kg/m³ DDAC | Weight loss % untreated weight loss |
|---|---|---|---|---|---|
| Untreated | 0 | 0 | 0 | 0 | 100 |
| Cu & Difenoconazole | 1.5 | 25:1 | 0 | 0 | 93 |
| | | | 0 | 1 | 0 |
| Cu & Metconazole | 1.5 | 50:1 | 0 | 0 | 85 |
| | | | 0 | 1 | 0 |
| Cu & Cyproconazole | 1.5 | 50:1 | 0 | 0 | 54 |
| | | 50:1 | 1 | 0 | 0 |
| | | 50:1 | 0 | 1 | 0 |

The data in the Table show that all of the combinations of the invention are effective against *Antrodia sinuosa*.

The invention claimed is:

1. A method for protecting wood or other cellulosic material from decay by copper-tolerant fungi, comprising applying thereto a biocidal metal compound, a 1,2,4-triazole compound and a salt containing a didecyl quaternary ammonium cation, wherein the biocidal metal compound is a biocidal copper compound.

2. The method as claimed in claim 1, wherein the wood or other cellulosic material is protected from decay by *Serpula himantioides, Antrodia* spp., *Gloeophyllum abietinum, Gloeophyllum sepiarium, Paxillus panuodes, Stereum hirsutum* and *Fomitopsis palustris*.

3. The method as claimed in claim 1, wherein the wood or other cellulosic material is protected from decay by *Serpula himantioides* and *Antrodia* spp.

4. The method as claimed in claim 1, wherein the wood or other cellulosic material is protected from decay by *Serpula himantioides*.

5. The method as claimed in claim 1, wherein the wood or other cellulosic material is protected from decay by *Antrodia vaillantii, Antrodia sinuosa* or *Antrodia radiculosa*.

6. The method as claimed in claim 1, wherein the biocidal metal compound, the 1,2,4-triazole and the salt containing the didecyldimethyl ammonium cation are in the same formulation.

7. The method as claimed in claim 1, wherein the salt containing the didecyldimethyl ammonium cation is applied to the wood-containing product separately from the biocidal metal compound and the 1,2,4-triazole compound.

8. The method as claimed in claim 1, wherein the 1,2,4-triazole is selected from compounds of formula (II):

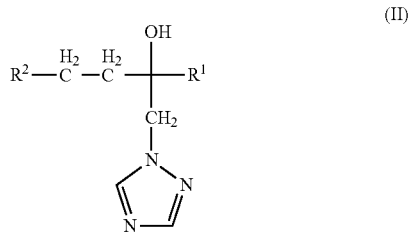

wherein
$R^1$ represents a branched or straight chain $C_{1-5}$ alkyl group and
$R^2$ represents a phenyl group optionally substituted by one or more substituents selected from halogen atoms, $C_{1-3}$ alkyl, $C_{1-3}$ alkoxy, phenyl or nitro groups; and
compounds of formula (III):

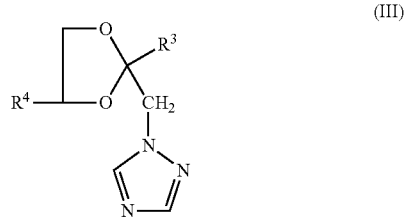

wherein
$R^3$ is as defined for $R^2$ above and
$R^4$ represents a hydrogen atom or a branched or straight chain $C_{1-5}$ alkyl group; or selected from the group consisting of triadimefon, triadimenol, triazbutil, cyproconazole, difenoconazole, fluquinconazole, flusilazole, uniconazole, diniconazole, bitertanol, hexaconazole, flutriafol, epoxyconazole, tetraconazole, penconazole, ipconazole, prothioconazole, metoconazole and mixtures thereof.

9. The method as claimed in claim 8, wherein the 1,2,4-triazole is selected from the group consisting of triadimefon, triadimenol, triazbutil, propiconazole, cyproconazole, difenoconazole, fluquinconazole, tebuconazole, flusilazole, uniconazole, diniconazole, bitertanol, hexaconazole, azaconazole, flutriafol, epoxyconazole, tetraconazole, penconazole, ipconazole, prothioconazole, metcoazole and mixtures thereof.

10. The method as claimed in claim 8, wherein the 1,2,4-triazole is selected from the group consisting of propiconazole, tebuconazole, and mixtures thereof.

11. The method as claimed in claim 1, wherein the biocidal metal compound further comprises a biocidal zinc compound.

12. The method as claimed in claim 1, wherein the biocidal copper compound contains copper (II).

13. The method as claimed in claim 1, wherein the biocidal copper compound is selected from the group consisting of basic copper carbonate, copper (II) acetate, copper (II) sulphate pentahydrate, copper (II) hydroxide, copper (II) oxide, copper (I) oxide, copper-HDO, and copper pyrithioneu.

14. The method as claimed in claim 12, wherein the biocidal copper compound is basic copper carbonate.

15. The method of claim 11, wherein the biocidal zinc compound is selected from the group consisting of zinc oxide, zinc carbonate, zinc borate and zinc pyrithione.

16. The method as claimed in claim 1, wherein the didecyl quaternary ammonium cation is represented by the compound of formula (I):

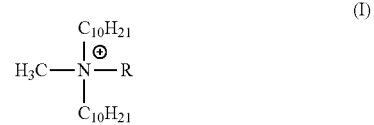

wherein
R denotes methyl or $(CH_2CH_2O)_mH$ where m is an integer from 1 to 20 typically from 1 to 8, preferably from 1 to 5 and more preferably from 3 to 5.

17. The method as claimed in claim 1, wherein the salt containing the didecyl quaternary ammonium cation is a propionate salt of a compound of formula (I)

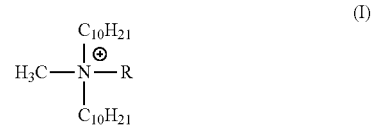

wherein
R denotes $(CH_2CH_2O)_mH$ and m is a range of integers of from 1 to 5.

18. The method as claimed in claim 1, wherein the didecyl quaternary ammonium cation is a didecyldimethyl ammonium cation.

19. The method as claimed in claim 18, wherein the salt containing a didecyldimethyl ammonium cation is didecyldimethyl ammonium chloride or didecyldimethyl ammonium carbonate/bicarbonate.

20. The method as claimed in claim 18, wherein the salt containing a didecyldimethyl ammonium cation is didecyldimethyl ammonium carbonate, didecyldimethyl ammonium bicarbonate, and mixtures thereof.

21. A method of enhancing the efficacy of a wood preservative formulation containing a biocidal metal compound and a 1,2,4-triazole against copper-tolerant fungi, comprising adding a salt containing a didecyl quaternary ammonium cation thereto, wherein the biocidal metal compound is a biocidal copper compound.

22. A method as claimed in claim 21, wherein the didecyl quaternary ammonium cation is a didecyldimethyl ammonium cation.

23. A method as claimed in claim 21, wherein the didecyl quaternary ammonium cation is a compound of formula (I) as defined in claim 16 wherein R denotes $(CH_2CH_2O)_mH$ and m is a range of integers of from 1 to 5.

24. A method according to claim 21, wherein the biocidal metal compound further comprises a biocidal zinc compound.

25. A wood preservative formulation comprising a biocidal metal compound, a 1,2,4-triazole and a proprionate salt of a compound of formula (I) as defined in claim 16 wherein R denotes $(CH_2CH_2O)_mH$ and m is a range of integers of from 1 to 5.

26. A wood preservative formulation comprising a biocidal metal compound, a 1,2,4-triazole and didecyldimethyl ammonium carbonate/bicarbonate, wherein the formulation does not contain any ammonia or alkanolamine and the biocidal metal compound is a biocidal copper compound.

27. A wood preservative formulation comprising a biocidal metal compound, a 1,2,4-triazole, a salt containing a didecyldimethyl ammonium cation, and an isothiazolone, wherein the biocidal metal compound is a biocidal copper compound.

28. A wood preservative formulation as claimed in claim 27, wherein the salt containing the didecyldimethyl ammonium cation is didecyldimethyl ammonium carbonate/bicarbonate.

29. A wood preservative formulation as claimed in claim 25, wherein the biocidal metal compound further comprises a biocidal zinc compound.

30. A wood preservative formulation as claimed in claim 25, wherein the 1,2,4-triazole is selected from compounds of formula (II):

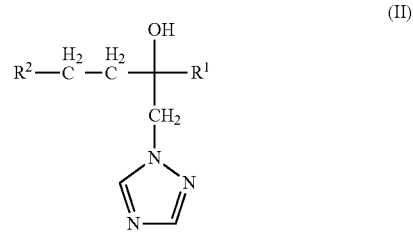

wherein
$R^1$ represents a branched or straight chain $C_{1-5}$ alkyl group and
$R^2$ represents a phenyl group optionally substituted by one or more substituents selected from halogen atoms, $C_{1-3}$ alkyl, $C_{1-3}$ alkoxy, phenyl or nitro groups; and
compounds of formula (III):

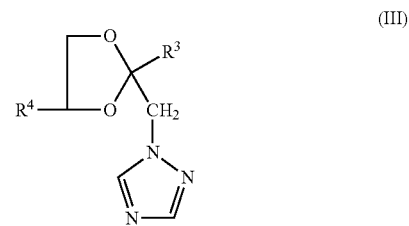

wherein
$R^3$ is as defined for $R^2$ above and
$R^4$ represents a hydrogen atom or a branched or straight chain $C_{1-5}$ alkyl group; or selected from the group consisting of triadimefon, triadimenol, triazbutil, cyproconazole, difenoconazole, fluquinconazole, flusilazole, uniconazole, diniconazole, bitertanol, hexaconazole, flutriafol, epoxyconazole, tetraconazole, penconazole, ipconazole, prothioconazole, metoconazole and mixtures thereof.

31. A wood preservative formulation as claimed in claim 25, wherein the 1,2,4-triazole is selected from the group consisting of difenoconazole, triadimefon, metconazole, cyproconazole, propiconazole and tebuconazole.

32. A wood preservative formulation as claimed in claim 25, wherein the 1,2,4-triazole is cyproconazole.

33. Wood or other cellulosic material which is impregnated with a formulation as defined in claim 25.

34. Wood or other cellulosic material which has been prepared by a method of claim 1.

* * * * *